United States Patent
Okuno et al.

(10) Patent No.: US 8,403,849 B2
(45) Date of Patent: Mar. 26, 2013

(54) ULTRASOUND DIAGNOSTIC APPARATUS

(75) Inventors: Yoshiyuki Okuno, Fussa (JP); Kenichi Nishina, Hachioji (JP); Katsuhiro Wakabayashi, Hachioji (JP); Jin Hiraoka, Sagamihara (JP); Satoshi Yoshida, Hachioji (JP); Masahiko Komuro, Hino (JP); Hironaka Miyaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/294,592

(22) Filed: Nov. 11, 2011

(65) Prior Publication Data

US 2012/0123273 A1  May 17, 2012

Related U.S. Application Data

(63) Continuation of application No. PCT/JP2011/066081, filed on Jul. 14, 2011.

(30) Foreign Application Priority Data

Aug. 6, 2010  (JP) ................................. 2010-177876

(51) Int. Cl.
*A61B 8/00*  (2006.01)

(52) U.S. Cl. ........ 600/437; 600/407; 600/441; 600/439; 600/443

(58) Field of Classification Search .................. 600/407, 600/437, 439, 441, 443
See application file for complete search history.

(56) References Cited

U.S. PATENT DOCUMENTS

| | | |
|---|---|---|
| 2004/0174203 A1 | 9/2004 | Wodnicki |
| 2004/0174773 A1 | 9/2004 | Thomenius et al. |
| 2004/0190377 A1 | 9/2004 | Lewandowski et al. |
| 2006/0084875 A1 | 4/2006 | Knight |
| 2008/0021324 A1 | 1/2008 | Seto |

FOREIGN PATENT DOCUMENTS

| | | |
|---|---|---|
| JP | 03-277353 | 12/1991 |
| JP | 2003-299648 | 10/2003 |
| JP | 2004-274756 | 9/2004 |
| JP | 2006-122659 | 5/2006 |
| JP | 2008-022887 | 2/2008 |
| JP | 2008-516683 | 5/2008 |
| WO | WO 01/21072 A1 | 3/2001 |
| WO | WO 2007/005036 A2 | 1/2007 |
| WO | WO 2007/086817 A1 | 8/2007 |

OTHER PUBLICATIONS

European Search Report dated Jun. 6, 2012 from corresponding European Patent Application No. EP 11 81 4427.8.

*Primary Examiner* — Tse Chen
*Assistant Examiner* — Joel Lamprecht
(74) *Attorney, Agent, or Firm* — Scully, Scott, Murphy & Presser, P.C.

(57) ABSTRACT

An ultrasound diagnostic apparatus includes: transmission and reception signal lines that send transmission and reception signals of ultrasound to a plurality of ultrasound transducers; signal determining portions near the ultrasound transducers and determine a selection signal for selecting an ultrasound transducer to be driven or a readout signal for reading out the selection signal, the selection signal being sent out in synchronization with a transmission signal for forming the transmission and reception signal, and couple the ultrasound transducer to be driven with the transmission and reception signal line according to a result of the determination; and direct current blocking/clipping circuits that block a direct current bias component superimposed on the transmission and reception signal and sent via the transmission and reception signal line, and clip a waveform with large amplitude. The transmission and reception signal line sends the transmission and reception signal with the selection signal or the readout signal.

16 Claims, 13 Drawing Sheets

FIG.12

(A) SET PATTERN A

| CLK No | TRANSMISSION/ RECEPTION | SELECTED C-MUT |
|---|---|---|
| 1 | TRANSMISSION | 8a |
| 2 | RECEPTION | 8a |
| 3 | TRANSMISSION | 8b |
| 4 | RECEPTION | 8b |
| ⋮ | ⋮ | ⋮ |

(B) SET PATTERN B

| CLK No | TRANSMISSION/ RECEPTION | SELECTED C-MUT |
|---|---|---|
| 1 | TRANSMISSION | 8a, 8b, 8c, 8d |
| 2 | RECEPTION | 8a |
| 3 | TRANSMISSION | 8a, 8b, 8c, 8d |
| 4 | RECEPTION | 8b |
| ⋮ | ⋮ | ⋮ |

ULTRASOUND DIAGNOSTIC APPARATUS

CROSS REFERENCE TO RELATED APPLICATION

This application is a continuation application of PCT/JP2011/066081 filed on Jul. 14, 2011 and claims benefit of Japanese Application No. 2010-177876 filed in Japan on Aug. 6, 2010, the entire contents of which are incorporated herein by this reference.

BACKGROUND OF THE INVENTION

1. Field of the Invention

The present invention relates to an ultrasound diagnostic apparatus that generates an ultrasound tomographic image by using ultrasound.

2. Description of the Related Art

Conventionally, ultrasound probes that use piezoelectric elements have been known, but in recent years, ultrasound probes that use broadband capacitive ultrasound transducers (called the C-MUTs) have been developed.

For example, as disclosed in Japanese Patent Application Laid-Open Publication No. 2008-516683 as a first conventional example, an ultrasound diagnostic apparatus that can be used by being connected with such ultrasound probes has been proposed. The C-MUT has a cavity on a silicon substrate and electrodes are provided over and under the cavity.

Bias voltages as well as ultrasound drive signals are applied onto these electrodes to vibrate a film at the top of the cavity, thereby transmitting ultrasound, and an echo signal that comes back is detected by the film at the top, so that the transmission and the reception of the ultrasound are achieved.

The C-MUT can be achieved using a MEMS (Micro Electro Mechanical Systems) process as well as the C-MUT can be smaller than a piezoelectric transducer because the size of one element is smaller. A technique has also been proposed in which the C-MUT, which can be smaller than a piezoelectric transducer, is connected with a drive shaft and used with an extra-fine ultrasound probe.

In addition, there are ultrasound diagnostic apparatuses that are implemented by arranging a plurality of ultrasound transducers and obtain ultrasound tomographic images by selecting some of the ultrasound transducers to perform transmission and reception. As a second conventional example, International Publication No. 2001/021072 discloses a structure in which a multiplexer is implemented at a probe distal end part close to ultrasound transducers.

SUMMARY OF THE INVENTION

An ultrasound diagnostic apparatus according to an aspect of the present invention includes: a plurality of ultrasound transducers; transmission and reception signal lines that send transmission and reception signals for transmitting and receiving ultrasound to the plurality of ultrasound transducers; signal determining portions that are provided close to the plurality of ultrasound transducers and determine a selection signal for selecting an ultrasound transducer to be driven or a readout signal for reading out the selection signal, the selection signal being sent out in synchronization with a transmission signal for forming the transmission and reception signal, and electrically couple the ultrasound transducer to be driven with the transmission and reception signal line in accordance with a result of the determination; and direct current blocking/clipping circuits that are provided in the signal determining portions, block a direct current bias component superimposed on the transmission and reception signal and sent via the transmission and reception signal line, and clip a waveform with large amplitude, wherein the transmission and reception signal line sends the transmission and reception signal with the selection signal or the readout signal, and wherein the direct current blocking/clipping circuit separates and extracts the selection signal or the readout signal superimposed on the transmission and reception signal line, at a position before a signal waveform of the transmission signal.

An ultrasound diagnostic apparatus according to another aspect of the present invention includes: a plurality of ultrasound transducers; transmission and reception signal lines that send transmission and reception signals for transmitting and receiving ultrasound to the plurality of ultrasound transducers; and signal determining portions that are provided close to the plurality of ultrasound transducers and determine a selection signal for selecting an ultrasound transducer to be driven, the selection signal being sent out in synchronization with a transmission signal for forming the transmission and reception signal, and electrically couple the ultrasound transducer to be driven with the transmission and reception signal line in accordance with a result of the determination, wherein the signal determining portion includes: a clipping circuit that clips a waveform of the transmission signal with large amplitude; a pulse counter that counts a number of pulses for forming the selection signal for selecting the ultrasound transducer to be driven; a judging portion that judges the ultrasound transducer to be driven using the number of the pulses counted by the pulse counter; and a gate circuit that opens and closes by a control signal of the judgement from the judging portion to apply the transmission signal to the ultrasound transducer to be driven, and wherein the transmission and reception signal line sends the transmission and reception signal with the selection signal.

BRIEF DESCRIPTION OF THE DRAWINGS

FIG. 12 is a diagram illustrating a table of a set pattern A and a table of a set pattern B stored in the LUT.

DETAILED DESCRIPTION OF THE PREFERRED EMBODIMENTS

Hereinafter, embodiments of the present invention will be described with reference to the drawings.

First Embodiment

Figure 1:
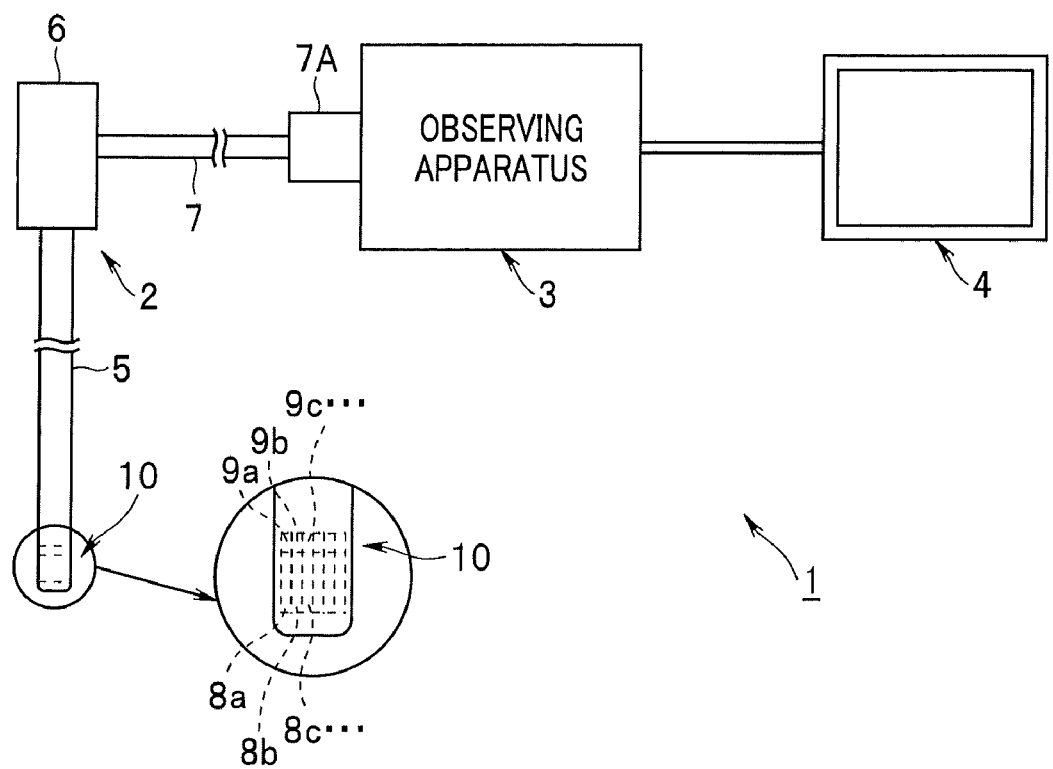
FIG. 1 is an external view of an ultrasound diagnostic apparatus of a first embodiment of the present invention.
Figure 2:
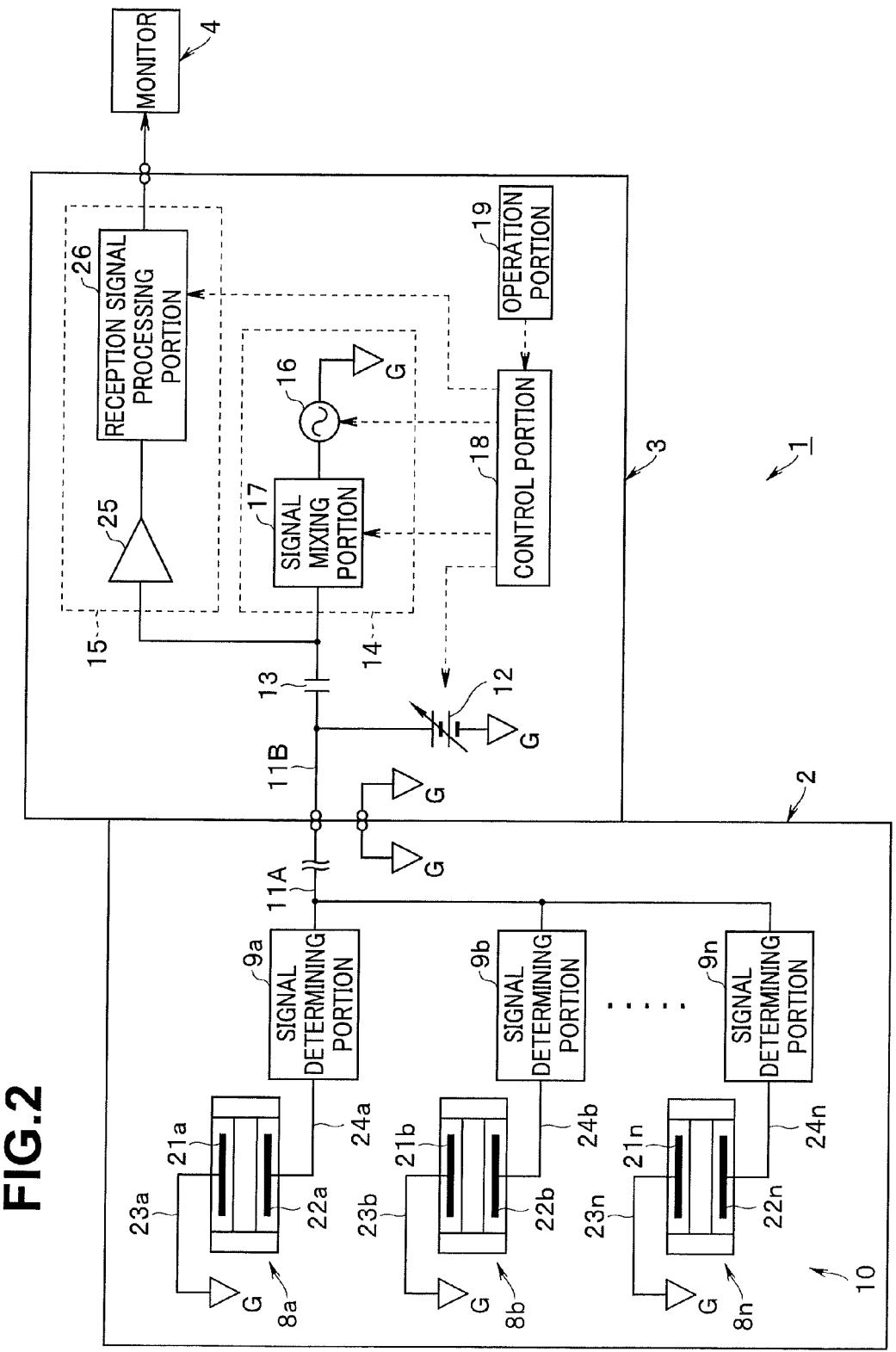
FIG. 2 is a block diagram illustrating a configuration of the ultrasound diagnostic apparatus of the first embodiment.

FIG. 1 illustrates an external view of an ultrasound diagnostic apparatus 1 of a first embodiment of the present invention, and FIG. 2 illustrates an example of an internal configuration of the apparatus 1.

As shown in FIG. 1, the ultrasound diagnostic apparatus 1 includes an ultrasound probe 2 provided with an ultrasound transducer array, an ultrasound observing apparatus (hereinafter, simply referred to as the observing apparatus) 3 with which the ultrasound probe 2 is connected, and a monitor 4 as a display device that is connected with the observing apparatus 3 and displays an ultrasound image.

The ultrasound probe 2 includes an elongated insertion portion 5 inserted into lumens such as blood vessels of an object to be examined, a grip portion 6 provided at a proximal end of the insertion portion 5, and a cable portion 7 extending from the grip portion 6. A connector 7A provided at an end portion of the cable portion 7 is detachably connected with a connector receiver (not shown) of the observing apparatus 3.

A distal end portion of the insertion portion 5 is provided with a plurality of ultrasound transducers, for example, an ultrasound transducer array 10 including a plurality of capacitive ultrasound transducers (Capacitive Micromachined Ultrasonic Transducers: abbreviated as the C-MUTs) $8a$, $8b$, $8c$, ..., and $8n$ as shown in the enlarged view of FIG. 1. In the cylindrical insertion portion 5, the plurality of rectangular board shaped C-MUTs $8a$, $8b$, ..., and $8n$ are arranged so as to form an annular ring on an inner side of an exterior cover which allows ultrasound to pass through.

Figure 3:
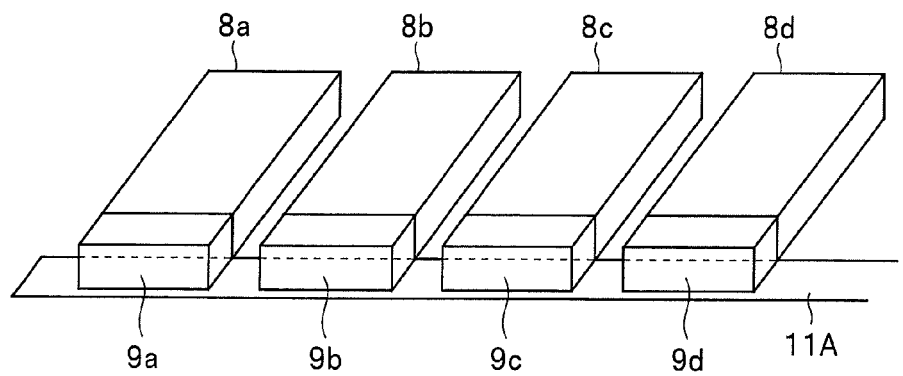
FIG. 3 is a diagram illustrating a part of an ultrasound transducer array in the first embodiment.

As shown in FIG. 2 and FIG. 3, the plurality of C-MUTs $8a$, $8b$, ..., and $8n$ constituting the ultrasound transducer array 10 are connected with a transmission and reception signal line 11A that sends transmission and reception signals and is inserted into the insertion portion 5 through signal determining portions $9a$, $9b$, ..., and $9n$ close to the plurality of C-MUTs $8a$, $8b$, ..., and $8n$.

As shown in FIG. 2, the transmission and reception signal line 11A is connected with one end of a transmission and reception signal line 11B in the observing apparatus 3 through the connector 7A.

The transmission and reception signal line 11B is connected with a DC bias outputting portion 12 that outputs a direct current (DC) bias voltage (simply abbreviated as the DC bias) as well as the line 11B is connected with a transmitting portion 14 and a receiving portion 15 through a DC blocking portion 13 having a capacitor that blocks the DC bias.

The transmitting portion 14 includes a transmission signal outputting portion (or a transmission signal generating portion) 16 that outputs or generates transmission signals and a signal mixing portion (or a signal superimposing portion) 17 that mixes (or superimposes) the transmission signals with transducer selection signals (abbreviated as the selection signals) for selecting the C-MUTs $8i$ (i=a, b, ..., and n) used to transmit and receive ultrasound.

Further, a control portion 18 controls an output timing of a transmission signal outputted from the transmission signal outputting portion 16 and an output timing of a selection signal from the signal mixing portion 17. The signal mixing portion 17 mixes (superimposes), under the control of the control portion 18, each selection signal for selecting a transducer before an output waveform of each transmission signal.

Figure 5:
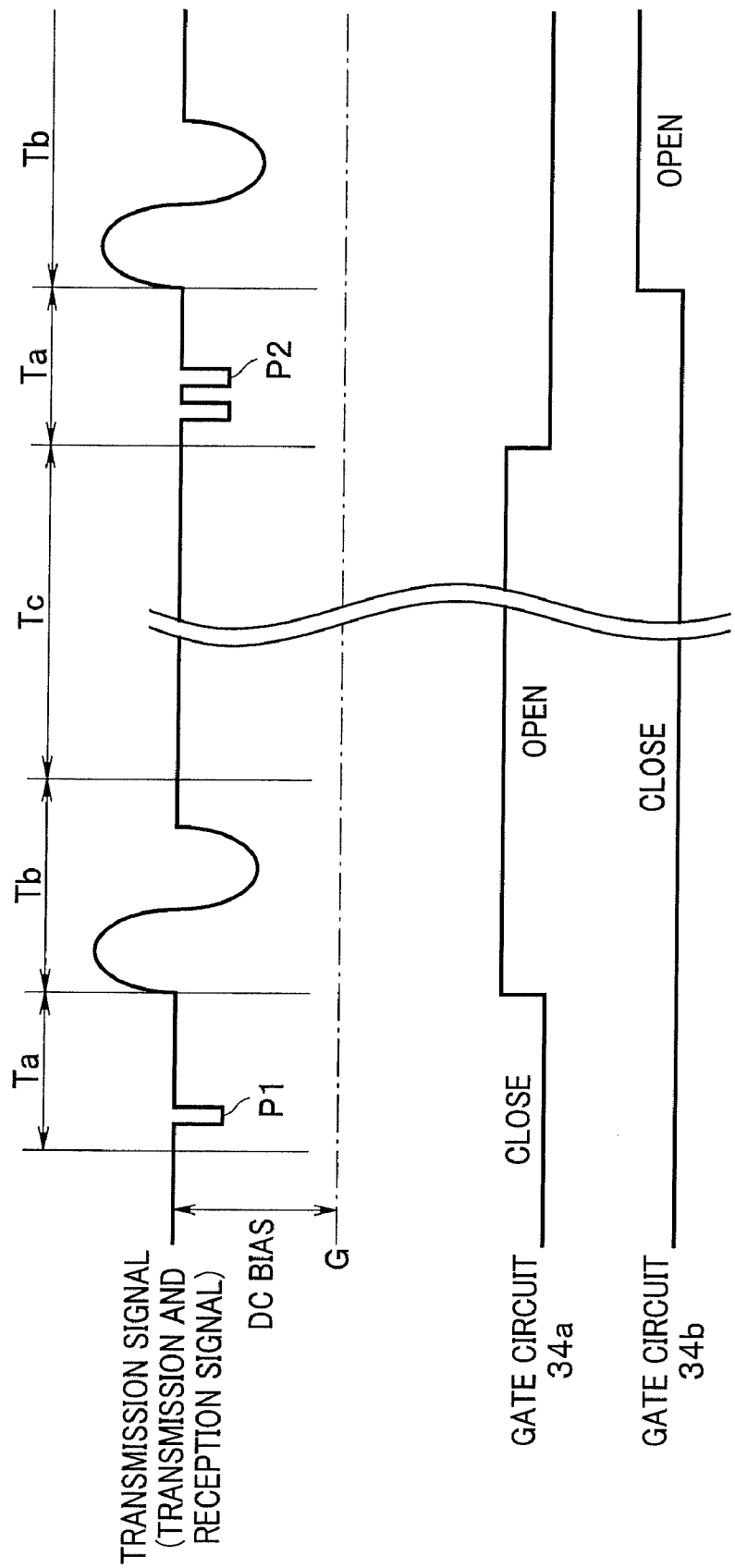
FIG. 5 is a diagram illustrating a waveform of a transmission signal inputted into the signal determining portion.

That is, in the present embodiment, transmission signals to be generated have a signal form in which selection signals in synchronization with the transmission signals are superimposed. The transmission signals on which the selection signals are superimposed are seen in FIG. 5 as described later.

The transmission signals on which the selection signals are superimposed are outputted from the transmitting portion 14. The DC biases from the DC bias outputting portion 12 are further superimposed on the transmission signals, and the transmission signals are transmitted to the transmission and reception signal line 11A of the ultrasound probe 2 via the transmission and reception signal line 11B. Then, the transmission signals sent via the transmission and reception signal line 11A are inputted into the signal determining portions $9i$ arranged at the distal end portion of the ultrasound probe 2.

In the present embodiment, in order to allow sequentially electrically driving the plurality of (n) C-MUTs $8a$, $8b$, ..., and $8n$ constituting the ultrasound transducer array 10 by n transmission signals, a selection signal for selecting each of the C-MUTs $8a$, $8b$, ..., and $8n$ is mixed (superimposed) before a signal waveform of each transmission signal.

Then, the signal determining portions $9i$ are provided on the transmission and reception signal line 11A that sends transmission and reception signals for transmitting and receiving the C-MUTs $8a$, $8b$, ..., and $8n$, and the signal determining portions $9i$ determine by the selection signal whether or not the transmission and reception signal is for the C-MUTs $8i$ to be driven. The signal determining portions $9i$ then open or close a gate circuits $34i$ described later, in accordance with a result of the determination.

As seen from FIG. 2, a signal line inserted into the ultrasound probe 2 is only one transmission and reception signal line 11A except for ground lines (GND lines) connected with the ground (terminals), so that a structure suitable to reduce an outer diameter of the insertion portion 5 of the ultrasound probe 2 is achieved.

As shown in FIG. 2, the C-MUT $8i$ has an upper electrode $21i$ and a lower electrode $22i$, and a cavity is made therebetween. The upper electrode $21i$ is connected with a ground (shown by G) through a signal line $23i$ and the lower electrode $22i$ is connected with one end of the signal determining portion $9i$ through a signal line $24i$. The other end of the signal determining portion $9i$ is connected with the common transmission and reception signal line 11A.

The C-MUT $8i$ applies a transmission signal between the upper electrode $21i$ and the lower electrode $22i$ with a DC bias voltage applied, thereby vibrating a film facing the cavity, for example, a film at the upper electrode 211 side to transmit ultrasound. Also, if ultrasound is received with a DC bias applied, the film facing the cavity vibrates to generate an ultrasound reception signal as an electrical signal.

The reception signal is inputted into the receiving portion 15 in the observing apparatus 3 through the signal determining portion 9i. The reception signal is amplified by an amplifier portion 25 constituting the receiving portion 15 and then inputted into a reception signal processing portion 26. The reception signal processing portion 26 performs signal processing to generate an ultrasound tomographic image from the reception signal and outputs video signals of the ultrasound tomographic image generated in the signal processing to the monitor 4. On the display of the monitor 4 the ultrasound tomographic image is displayed.

The control portion 18 in the observing apparatus 3 also controls the DC bias outputting portion 12 and the reception signal processing portion 26. Also, an operation portion 19 is installed with which various operation signals are inputted to control the operation of the observing apparatus 3 through the control portion 18.

The present embodiment is the ultrasound diagnostic apparatus 1 including the plurality of C-MUTs 8a, 8b, . . . , and 8n as a plurality of ultrasound transducers, and includes the transmission and reception signal line 11A that sends transmission and reception signals for transmitting and receiving ultrasound to and from the plurality of ultrasound transducers.

Also, the ultrasound diagnostic apparatus 1 includes signal determining portions 9a, 9b, . . . , and 9n that are close to the plurality of ultrasound transducers and determine a selection signal for selecting an ultrasound transducer to be driven, the selection signal being sent out in synchronization with a transmission signal forming the transmission and reception signal, and electrically couple the ultrasound transducer to be driven to the transmission and reception signal line 11A in accordance with a result of the determination, and the transmission and reception signal line 11A sends the selection signal (mixed) with the transmission and reception signal.

In a third embodiment described later, a readout signal (a replacement for the selection signal) superimposed on the transmission signal is sent out and a signal determining portion 61 determines a CLK for LUT as a readout signal. Then, in accordance with the readout signal, data of the corresponding selection signal is read out from a selection look-up table portion in which the selection signals for selecting ultrasound transducers performing transmission and reception are pre-stored.

FIG. 3 illustrates an example of arrangement of C-MUTs 8i (FIG. 3 shows the case of i=a, b, c and d) and signal determining portions 9i. The signal determining portions 9i are contiguous to the C-MUTs 8i. It should be noted that the signal determining portions 9i may be integrated with the contiguous C-MUTs 8i. The respective signal determining portions 9i are provided on the common transmission and reception signal line 11A.

Figure 4:
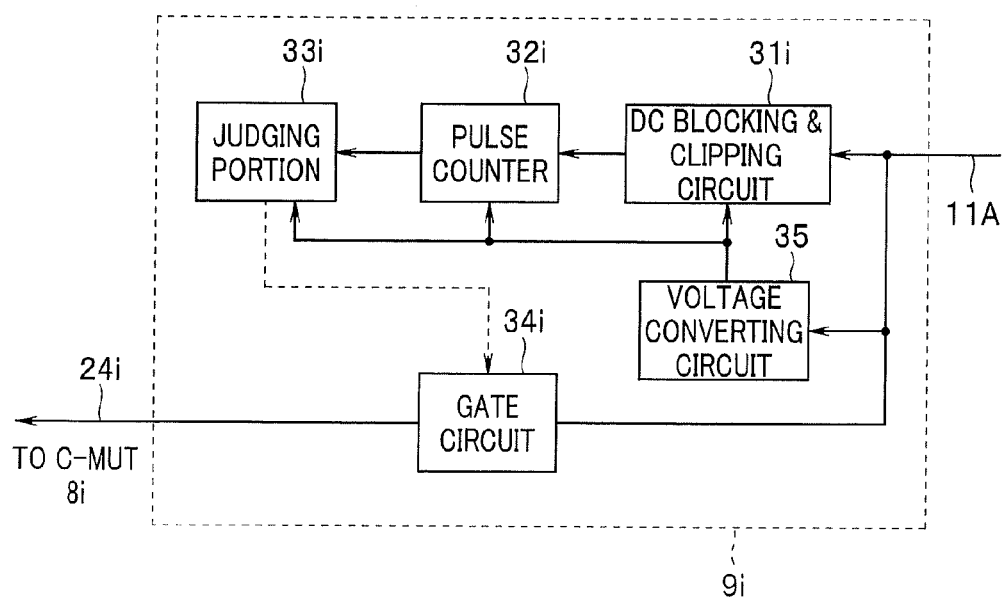
FIG. 4 is a block diagram illustrating a configuration of a signal determining portion.

The signal determining portion 9i has a configuration as illustrated in FIG. 4. FIG. 5 illustrates a transmission signal (a transmission and reception signal) inputted into the signal determining portion 9i. The transmission signal forming the transmission and reception signal shown in FIG. 5 is generated under the control of the above-described control portion 18.

As seen from the following description, a transmission and reception signal includes a transmission signal in a selection code time period Ta and a transmission time period Tb shown in FIG. 5, and a reception signal in a reception time period Tc following the transmission time period Tb. Also, as seen from FIG. 5, the period for the transmission signal is time-divided into the selection code time period Ta and the transmission time period Tb, and a transducer selection code as a selection signal and a transmission signal are sent via the transmission and reception signal line 11A.

As shown in FIG. 5, a transmission signal inputted into the signal determining portion 9i via the transmission and reception signal line 11A includes the selection code time period Ta (as a selection signal time period) in which a pulse as a transducer selection code as a selection signal for selecting an ultrasound transducer to be driven that is actually used for transmission and reception is superimposed on a DC bias, and the transmission time period Tb having a transmission signal for driving the selected C-MUT 8i to be driven. Further, after the transmission time period Tb, only the DC bias is applied onto the transmission and reception signal line 11A, and the reception time period Tc starts in which a reception signal is received.

In the selection code time period Ta, a transducer selection code as a selection signal for determining the C-MUT 8i to be driven is inserted in, at a predetermined timing, before a waveform of transmission signal. As an example of the foregoing, as an example of a selection code signal inserted in the selection code time period Ta, FIG. 5 shows the case of a pulse having a predetermined pulse width.

As shown in FIG. 5, in the selection code time period Ta, in order to drive the first C-MUT 8a by a transmission signal, one pulse as a transducer selection code P1 corresponding to the first C-MUT 8a is time-divided and superimposed before a signal waveform of the transmission signal.

In this case, one pulse having a predetermined pulse width, for example, a negative pulse, is placed before the waveform of the transmission signal. After the transmission time period Tb and the reception time period Tc, in order to drive the second C-MUT 8b by the transmission signal, a transducer selection code P2 of two pulses is placed before a waveform of the transmission signal. Next to the transducer selection code P2 of two pulses, although not shown, transducer selection codes of three pulses, four pulses, . . . , and n pulses follow.

The signal determining portion 9i shown in FIG. 4 includes a DC blocking and clipping circuit 31i into which the transmission signal is inputted and a gate circuit 34i.

The DC blocking and clipping circuit 31i includes a DC blocking circuit that blocks a DC bias component in a selection signal and a clipping circuit that clips a transmission signal with large amplitude to extract only a pulse that forms a selection signal with small amplitude. It should be noted that the DC blocking and clipping circuit 31i is not limited to a configuration in which a DC blocking circuit is integrated with a clipping circuit, and the DC blocking circuit may be separated from the clipping circuit.

A pulse (forming a selection signal) extracted by the DC blocking and clipping circuit 31i is inputted into a pulse counter 32i, and the pulse counter 32i counts the number of inputted pulses and outputs the number to a judging portion (or a determining portion) 33i.

The judging portion 33i judges (determines) whether or not the number agrees with a count number set beforehand in accordance with the C-MUT 8i contiguous to the signal determining portion 9i. For example, in a judging portion 33a contiguous to the first C-MUT 8a shown in FIG. 3, 1 is preset as a count number for judgement. Then, as shown in FIG. 5, if the transducer selection code P1 with the number of pulses being 1 is inputted, since the number of pulses agrees with the preset count number, the judging portion 33a judges that the transducer selection code P1 is a selection signal for selecting an ultrasound transducer to be driven which is used to transmit and receive ultrasound.

If the judging portion 33$i$ judges that the code is a selection signal for driving the C-MUT 8$i$ to be driven, the judging portion 33$i$ applies a control signal to a gate opening and closing control terminal (simply referred to as the control end) of the gate circuit 34$i$ to control the opening and closing of the gate of the gate circuit 34$i$, that is, to switch the gate from closed to open.

It should be noted that in FIG. 4, the DC blocking and clipping circuit 31$i$, the pulse counter 32$i$, the judging portion 33$i$, and the gate circuit 34$i$, which constitute the signal determining portion 9$i$, use the DC biases from the DC bias outputting portion 12 as an operating power supply.

For example, a DC bias is converted by a voltage converting circuit 35 in the signal determining portion 9$i$ into a predetermined power supply voltage used to operate the pulse counter 32$i$, the judging portion 33$i$, and the gate circuit 34$i$. Then, the predetermined power supply voltage is supplied to the pulse counter 32$i$, the judging portion 33$i$, and the gate circuit 34$i$. The voltage converting circuit 35 is composed of a known three-terminal constant voltage integrated circuit (IC) (not shown).

In the present embodiment, because a DC bias is used as power supply, it is not necessary to insert a power supply line into the ultrasound probe 2 in order to operate the signal determining portion 9$i$. In other words, the transmission and reception signal line 11A also functions as a power supply line for sending power supply in order to operate the signal determining portion 9$i$.

It should be noted that in FIG. 4, although each signal determining portion 9$i$ has a voltage converting circuit 35, for example, only one signal determining portion 9$a$ may have a voltage converting circuit 35 and the voltage converting circuit 35 may supply power supply to the pulse counters 32$a$ to 32$n$, the judging portions 33$a$ to 33$n$, and the gate circuits 34$a$ to 34$n$ of all the signal determining portions 9$a$ to 9$n$.

As described above, a transmission signal is inputted into (one terminal of) the gate circuit 34$i$, and if a control signal is applied from the judging portion 33$i$, the gate circuit 34$i$ opens the gate. Then, the gate circuit 34$i$ outputs a signal inputted into the one terminal of the gate circuit 34$i$ to the other terminal.

In other words, the gate circuit 34$i$ causes one terminal and the other terminal to enter a conductive state, that is, an electrically connected state in response to a control signal applied to a control end. In this case, a transmission signal offset by an inputted DC bias component is sent out to the C-MUT 8$i$. It should be noted that the gate circuit 34$i$ is set to close when the gate circuit 34$i$ receives a start signal of a next selection signal time period Ta.

Therefore, as shown in FIG. 5, if the gate circuit 34$i$ is opened in the transmission time period Tb, the opened state is maintained for the reception time period Tc. That is, the gate circuit 34$i$ is opened to send out a transmission signal to the C-MUT 8$i$ to be driven as well as the gate circuit 34$i$ maintains the open to send out a reception signal received by the C-MUT 8$i$ used for the transmission, to the observing apparatus 3 via the transmission and reception signal line 11A in the reception time period Tc.

FIG. 5 illustrates gate opening and closing of the gate circuits 34$a$ and 34$b$ as a specific example. It should be noted that an L level indicates closed and an H level indicates open. The transmission signal is applied onto the C-MUT 8$i$ via the gate circuit 34$i$, and thereby the C-MUT 8$i$ transmits ultrasound.

As described above, in the ultrasound transducer array 10, since the C-MUTs 8$a$, 8$b$, . . . , and 8$n$ are arranged to form an annular ring shape, and selection signals with the number of pulses set as 1, 2, . . . , and 8$n$ are placed before the transmission signals, the C-MUTs 8$a$, 8$b$, . . . , and n are sequentially selected and driven by the transmission signals to radially transmit ultrasound (radially scan) by the driven C-MUT 8$i$.

Then, if the distal end portion of the ultrasound probe 2 is inserted in lumen sites in the object to be examined, such as a bile duct and a pancreatic duct, the C-MUT 8$i$ radially transmit ultrasound to a duct wall around the distal end portion of the ultrasound probe 2. An ultrasound echo reflected from a part in which acoustic impedance is changed is received by the C-MUT 8$i$ used for the transmission.

The received ultrasound echo is changed by the C-MUT 8$i$ into an electrical reception signal and passes through the transmission and reception signal lines 11A and 11B. Then, the DC bias component of the electrical signal is blocked by the DC blocking portion 13 and the signal is inputted into the amplifier portion 25. After the amplifier portion 25 amplifies the reception signal, an ultrasound tomographic image from the radial scan is generated by the reception signal processing portion 26 and displayed on the monitor 4.

FIG. 6(A) illustrates a scheme in which the C-MUTs 8$a$, 8$b$, . . . , and 8$n$ constituting the ultrasound transducer array 10 in the present embodiment are sequentially changed over and driven to perform radial electronic scanning. FIG. 6(B) schematically illustrates a conventional example of a scanning scheme that uses a drive shaft 41.

As described above, the present embodiment adopts the scheme in which selection signals are superimposed on transmission signals and C-MUTs 8$i$ to be driven are sequentially selected (changed over) by the selection signals to perform radial electronic scanning on ultrasound.

In the conventional example shown in FIG. 6(B), as an ultrasound transducer on the drive shaft 41, for example, a C-MUT 42 is mechanically driven to rotate in an arrow direction to mechanically scan ultrasound.

Figure 6:
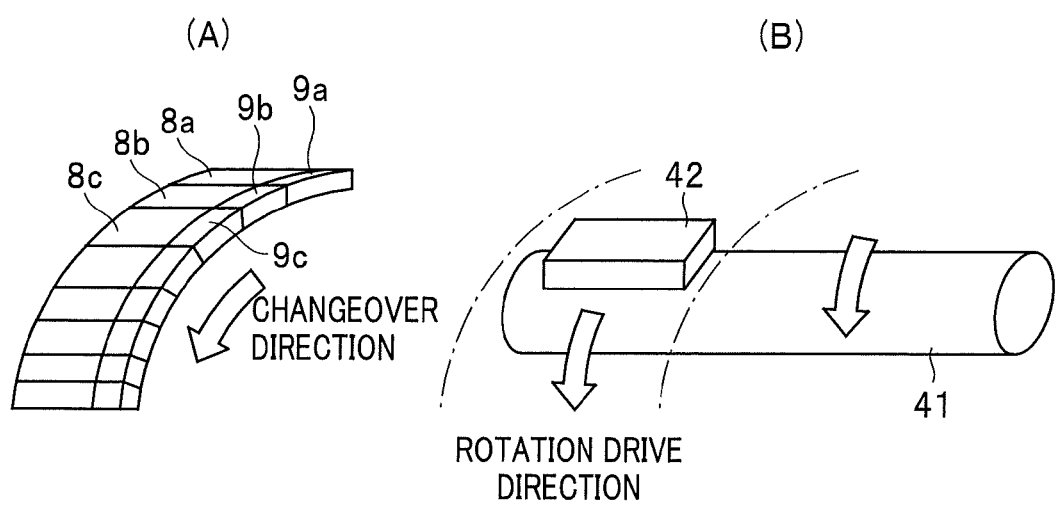
FIG. 6 is an explanation diagram showing that a plurality of C-MUTs being a plurality of ultrasound transducers constituting the ultrasound transducer array are changed over so that the C-MUTs are driven to be electrically selected one after another and an explanation diagram of a conventional example in which one ultrasound transducer is mechanically driven to rotate by a drive shaft to scan ultrasound.

In the present embodiment, without the C-MUT 42 shown in FIG. 6(B) being mechanically driven to rotate, selected C-MUTs can be changed over one after another in an arrow direction of FIG. 6 (A), like 8$a$, 8$b$, 8$c$, and so on, to radially scan ultrasound and obtain an ultrasound tomographic image by the radial scanning.

As a result, according to the present embodiment, a flow of an image caused by the poor followability of the drive shaft 41 can be prevented from occurring, and an ultrasound tomographic image with high quality can be obtained.

Furthermore, in spite of such an electronic scanning scheme in which C-MUTs 8$i$ are changed over and driven, the transmission and reception signal line 11A sends transmission and reception signals as well as functions as a signal line that sends selection signals.

Thus, according to the present embodiment, the ultrasound transducer array 10 can be driven by only one transmission and reception signal line 11A except for the ground lines, so that the number of signal lines inserted into the ultrasound probe 2 can be reduced.

Thus, according to the present embodiment, since the number of signal lines can be reduced, advantageously, the insertion portion 5 of the ultrasound probe 2 can be made thin, that is, an outer diameter of the insertion portion 5 can be reduced.

In addition, the present embodiment can be applied to use in which for example, the insertion portion 5 of the ultrasound probe 2 is made thin and inserted in thinner lumens. That is, the present embodiment can be widely applied.

Second Embodiment

Figure 7:
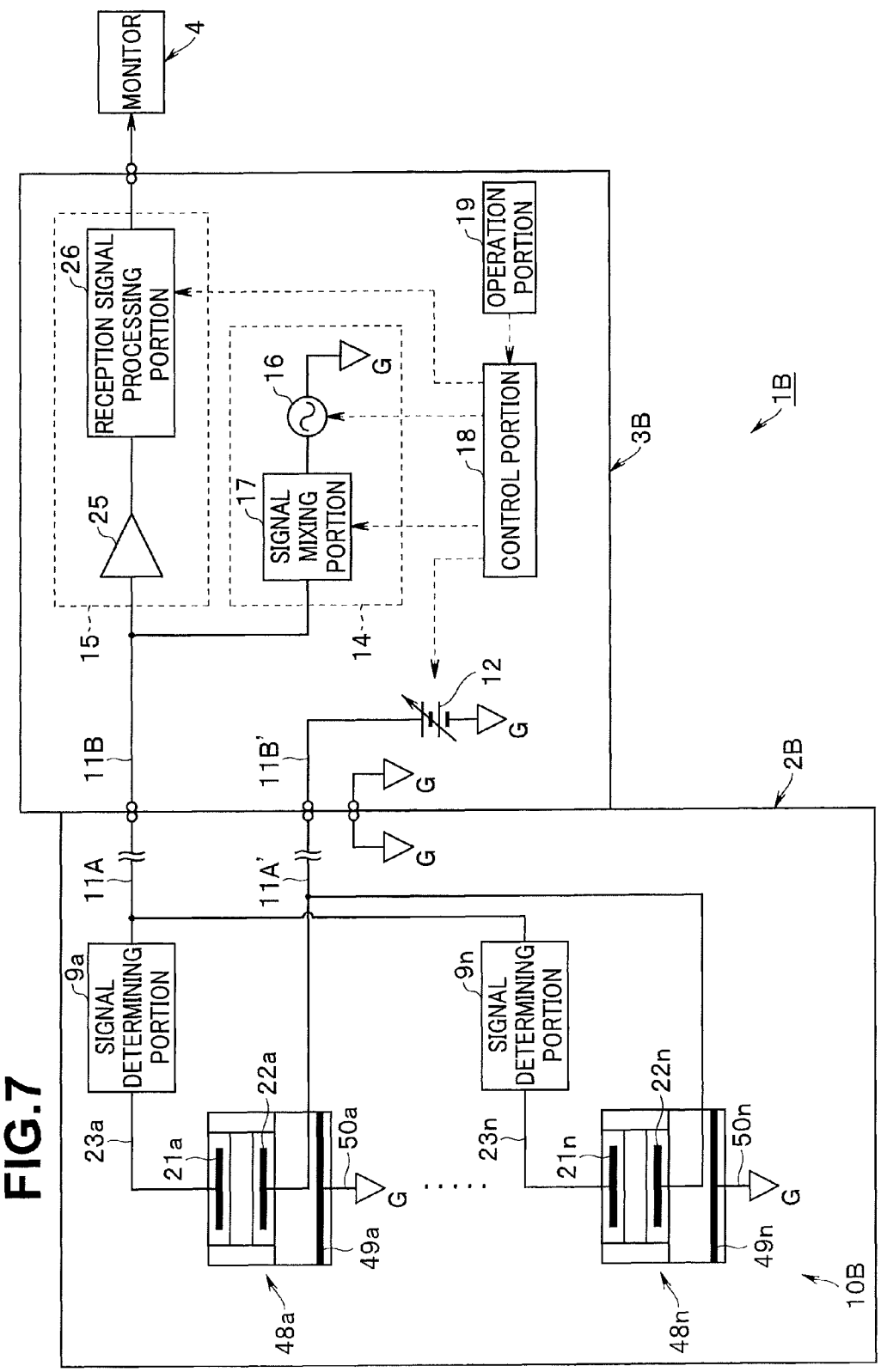
FIG. 7 is a block diagram illustrating a configuration of an ultrasound diagnostic apparatus of a second embodiment of the present invention.

FIG. 7 illustrates a configuration of an ultrasound diagnostic apparatus 1B of a second embodiment of the present invention. The ultrasound diagnostic apparatus 1B includes an ultrasound probe 2B, an observing apparatus 3B, and a monitor 4.

The C-MUT 8$i$ in the ultrasound transducer array 10 of the above-described first embodiment has two electrodes.

On the other hand, a plurality of C-MUTs 48$a$, 48$b$, ..., and 48$n$ (in FIG. 7, simply denoted by the C-MUTs 48$a$, ..., and 48$n$) constituting an ultrasound transducer array 10B in the present embodiment include the following three electrodes: an upper electrode 21$i$, a lower electrode 22$i$, and a ground electrode (GND electrode) 49$i$ being near the lower electrode 22$i$ and connected with a ground.

A signal line 23$i$ connected with the upper electrode 21$i$ of the C-MUT 48$i$ is connected with a transmission and reception signal line 11A through a signal determining portion 9$i$, and the lower electrode 22$i$ is connected with a DC bias signal line 11A' inserted into the ultrasound probe 2B. The GND electrode 49$i$ is each connected with the ground via a GND line 50$i$.

The transmission and reception signal line 11A is connected with a transmitting portion 14 and a receiving portion 15 via a transmission and reception signal line 11B in the observing apparatus 3B (without the DC blocking portion 13 of FIG. 2 being inserted) and the DC bias signal line 11A' is connected with a DC bias outputting portion 12 via a DC bias signal line 11B' in the observing apparatus 3B. The other components are the same as those in FIG. 2.

Thus, the C-MUT 48$i$ in the present embodiment includes the upper electrode 21$i$ to which transmission and reception signals are applied, the lower electrode 22$i$ to which DC bias voltages are applied, and the GND electrode 49$i$ set at the GND potential. The second embodiment is different from the first embodiment illustrated in FIG. 1 in the point that an electrode onto which DC biases are applied is different from an electrode onto which transmission and reception signals are applied.

Therefore, a transmission signal outputted from a transmission signal outputting portion 16 is mixed with a selection signal in a signal mixing portion 17, and sent out via the transmission and reception signal lines 11B and 11A to the signal determining portion 9$i$.

In the signal determining portion 9$i$, if a C-MUT 48$i$ is selected, the transmission signal is sent out to the upper electrode 21$i$ of the C-MUT 48$i$ to cause a film at the upper electrode 21$i$ to send out ultrasound.

The C-MUT 48$i$ outputs a reception signal obtained from ultrasound caused by the transmission signal transmitting ultrasound and reflected from an object to be examined, to the receiving portion 15 via the signal determining portion 9$i$, and the transmission and reception signal lines 11A and 11B. The receiving portion 15 amplifies the reception signal by an amplifier portion 25, imaging the reception signal at a reception signal processing portion 26, and displays the reception signal on the monitor 4 as an ultrasound tomographic image.

Figure 8:
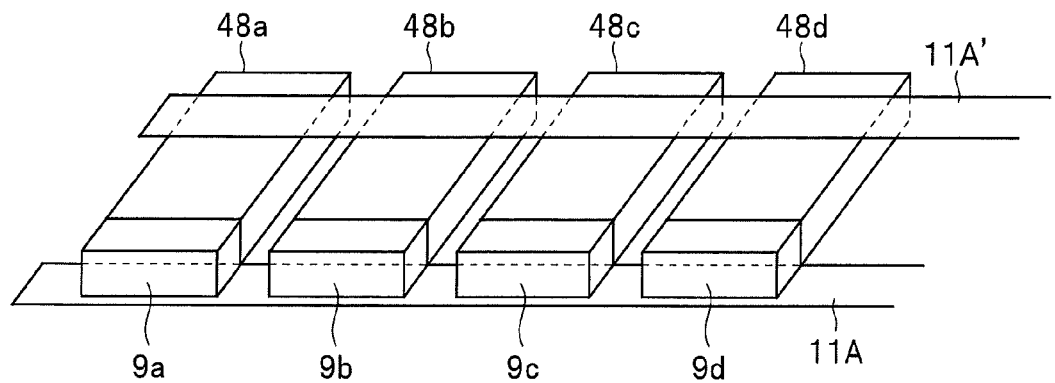
FIG. 8 is a diagram illustrating a part of an ultrasound transducer array in the second embodiment.

Here, an example of arrangement relationship between three-electrode-type C-MUTs 48$i$ and signal determining portions 9$i$ is shown in FIG. 8. The signal determining portions 9$a$ to 9$d$ are on the transmission and reception signal line 11A and are connected with the C-MUTs 48$a$ to 48$d$, respectively.

The opposite side of the C-MUTs 48$a$ to 48$d$ is connected with the DC bias signal line 11A', which is connected with the lower electrodes 22$a$ to 22$d$ of the C-MUTs 48$a$ to 48$d$ and with the DC bias outputting portion 12. It should be noted that although not shown in FIG. 8, a GND line 50 connected with the GND electrode 49$i$ is disposed contiguous to the DC bias signal line 11A'. Also, the DC bias signal line 11A' is connected with the signal determining portion 9$i$ to supply power thereto (not shown).

Figure 9:
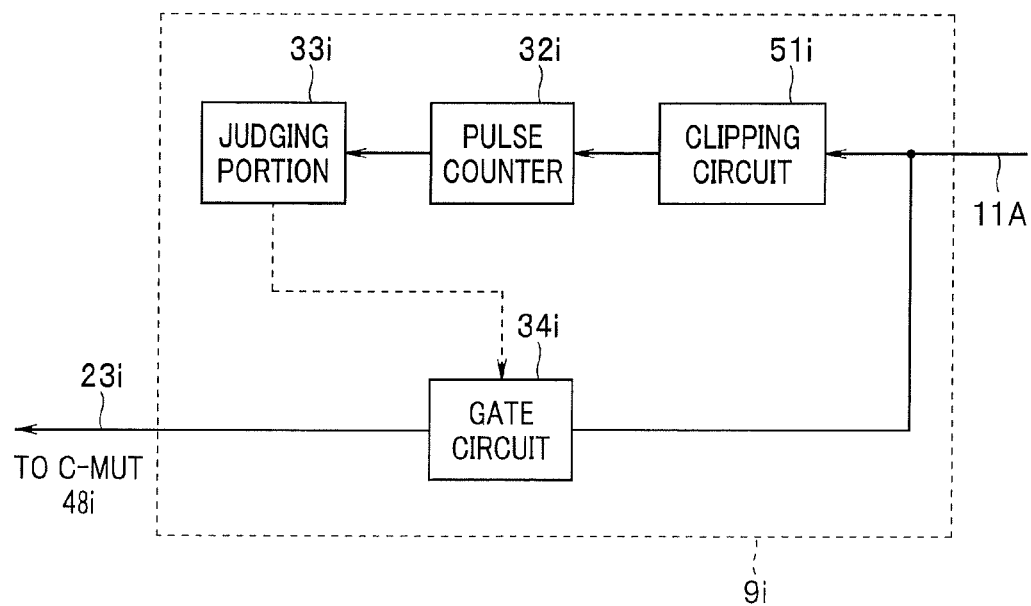
FIG. 9 is a block diagram illustrating a configuration of a signal determining portion.

A configuration of the signal determining portion 9$i$ in the present embodiment is shown in FIG. 9. In the configuration of the signal determining portion 9$i$ shown in FIG. 4, the DC blocking and clipping circuit 311 has been adopted in order to take a selection signal out of a transmission signal. On the other hand, the signal determining portion 9$i$ in FIG. 9 is different from that in FIG. 4 in the point that the signal determining portion 9$i$ in FIG. 9 does not have a DC blocking circuit part but uses a clipping circuit 51$i$ that clips a waveform of a transmission signal with large amplitude and extracts a selection signal in order to take a selection signal out of a transmission signal.

In the case of the three-electrode-type configuration, because a DC bias component is not superimposed on a transmission signal, processing for DC blocking is not needed. Thus, the clipping circuit 51$i$ may be a diode-like device. Further, a reception signal can be processed without being passed through the DC blocking portion 13 of the first embodiment, effects of the DC blocking portion 13 such as a capacitor (on a signal waveform at a low frequency side) can be reduced.

The other configurations and operations are the same as those in the first embodiment. Further, also in the present embodiment, because the transmission and reception signal line 11A also functions as a signal line that sends selection signals, the ultrasound transducer array 10 can be driven by using only one transmission and reception signal line 11A and one DC bias signal line 11A', except for the ground lines. Therefore, advantageously, the number of signal lines inserted into the ultrasound probe 2 can be reduced, so that the insertion portion 5 of the ultrasound probe 2 can be made thin, that is, an outer diameter of the insertion portion 5 can be reduced. Therefore, the present embodiment can be widely applied.

Third Embodiment

In the foregoing embodiments, the case has been described in which one C-MUT that is actually used for transmission and reception, i.e., only a single C-MUT is selected by a selection signal. In the present embodiment, the case in which a plurality of ultrasound transducers are selected at a time is described.

Figure 10:
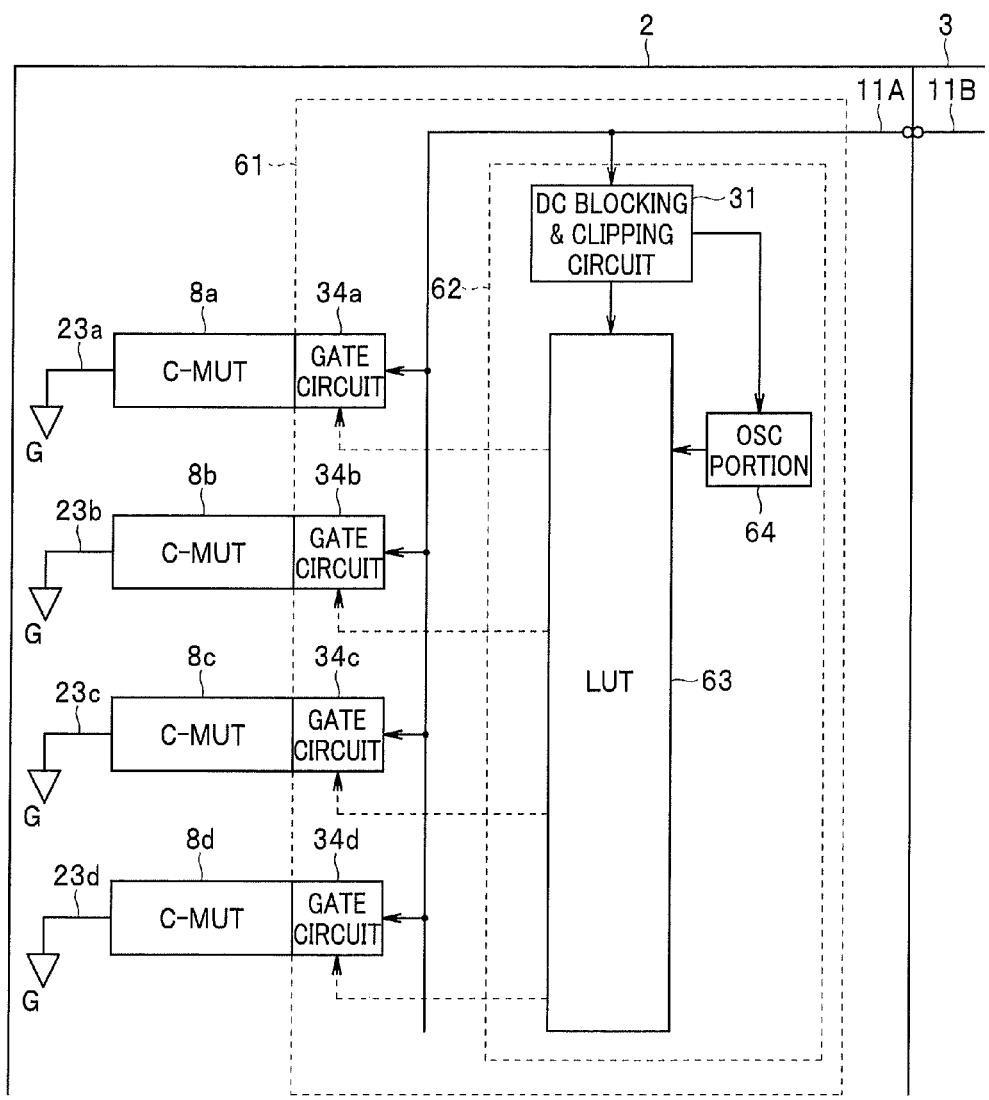
FIG. 10 is a block diagram illustrating a configuration around a signal determining portion in a third embodiment of the present invention.

FIG. 10 illustrates a configuration of a signal determining portion 61 in which for example, a plurality of C-MUTs (here, four C-MUTs 8$a$ to 8$d$) in the ultrasound probe 2 shown in FIG. 1 can be selected by selection signals. It should be noted that the present embodiment can be applied in the same manner to the case of more than four C-MUTs.

As in the case described in the first embodiment, a common transmission and reception signal line 11A is connected with (a lower electrode 22$i$ of) a C-MUT 8$i$ via each gate circuit 34$i$, and (an upper electrode 21$i$ of) each C-MUT 8$i$ is connected with the ground via a signal line 23$i$.

In the first embodiment, each gate circuit 34$i$ is opened and closed (more specifically, from closed to open) by a control signal from an individual signal determining portion 9$i$, but in the present embodiment, one selection circuit 62 controls the opening and closing of each of, for example, four gate circuits 34a to 34d.

In other words, in the present embodiment, the signal determining portion 61 includes the gate circuits 34a to 34d connected and contiguous to the C-MUTs 8a to 8d, and one selection circuit 62 that controls the gate opening and closing of the plurality of gate circuits 34a to 34d.

As shown in FIG. 10, the selection circuit 62 includes a DC blocking and clipping circuit 31, a look-up table (abbreviated as the LUT) 63 as a selection look-up table portion in which information of a selected C-MUT 8i is stored, and a timing generating oscillation portion (abbreviated as the OSC portion) 64 for operating the LUT 63.

It should be noted that as described below, the LUT 63 stores (data of) selection signals for selecting a C-MUT 8i to be driven before the C-MUT 8i is actually driven by a transmission signal.

Operations including the selection circuit 62 will be described using timing diagrams in FIG. 11. FIG. 11(A) illustrates a timing diagram for explaining an operation to store a transducer selection code 71 as a selection signal in the LUT 63 of the selection circuit 62 using, for example, the transmission and reception signal line 11A.

The observing apparatus 3 sends out a trigger 72 for a transducer selection code via the transmission and reception signal line 11A, and thereby the DC blocking and clipping circuit 31 of the selection circuit 62 judges that the transducer selection code 71 is sent out in synchronization with a timing that follows the trigger 72 for transducer selection code. Then, the DC blocking and clipping circuit 31 sends a judgement signal to the OSC portion 64, and the OSC portion 64 generates a timing signal for storing the transducer selection code 71 in the LUT 63.

The transducer selection code 71 sent out via the transmission and reception signal line 11A after the trigger 72 for transducer selection code is stored in the LUT 63 in synchronization with the timing signal of the OSC portion 64.

In this manner, the LUT 63 stores the data of the transducer selection code 71 as a selection signal for selecting and driving the C-MUTs 8a to 8d. In the present embodiment, after the data of a selection signal is stored in the LUT 63 in such a manner, ultrasound is actually transmitted or received. For example, the transmitting portion 14 shown in FIG. 1 mixes a clock for LUT (abbreviated as the CLK for LUT) 73 as a readout signal for reading out a selection signal stored in the LUT 63, at a predetermined timing before a signal waveform of a transmission signal.

If the C-MUTs 8a to 8d are actually driven, the transmitting portion 14 prefixes the CLK 73 for LUT to a transmission signal shown in FIG. 11(B) and sends out the signal via the transmission and reception signal line 11A to the signal determining portion 61.

It should be noted that in the first embodiment, as shown in FIG. 5, the number of pulses of the transducer selection code has changed like P1, P2, and so on, but in the present embodiment, the same one CLK 73 for LUT is used.

In FIG. 11(B), the CLKs 73 for LUT are placed instead of the transducer selection code in the selection code time period Ta of FIG. 5. Because also in the time period in which the CLKs 73 for LUT are placed, data of a selection signal is read out from the LUT 63 and an ultrasound transducer to be driven is selected by the read-out selection signal, the period is denoted as the selection signal time period Ta'.

Further, in FIG. 11(B), the CLK 73 for LUT is placed at a timing position of the start of the reception time period Tc following the transmission time period Tb, and the C-MUTs 8a to 8d for receiving ultrasound in the reception time period Tc in synchronization with the timing of this CLK 73 for LUT are selectively set. That is, the first CLK 73 for LUT placed before the signal waveform of the transmission signal in the transmission time period Tb is used as a readout signal for selecting an ultrasound transducer for transmission and the second CLK 73 for LUT placed after the signal waveform of the transmission signal is used as a readout signal for selecting an ultrasound transducer for reception.

As shown in FIG. 11(B), if the CLK 73 for LUT placed before the signal waveform of the transmission signal is transmitted, the DC blocking and clipping circuit 31 sends a signal in synchronization with the timing of the CLK 73 for LUT to the OSC portion 64. The OSC portion 64 applies a clock corresponding to the CLK 73 for LUT onto the LUT 63.

In response to the application of the clock corresponding to the CLK 73 for LUT from the OSC portion 64, in accordance with the data of the selection signal stored in the LUT 63, the LUT 63 outputs a control signal for controlling the (gate) opening and closing of the gate circuits 34a to 34d contiguous to the C-MUTs 8a to 8d, respectively. Then, in accordance with the data of the selection signal stored in the LUT 63, the gate circuits 34a to 34d switch from closed to open. In this case, the opened gate circuit maintains the opened state until a next CLK 73 for LUT (as a readout signal) is inputted.

It should be noted that a scheme may be adopted in which the CLK 73 for LUT has a predetermined pulse width and the opening and closing of the gate circuits 34a to 34d is properly operated only if the DC blocking and clipping circuit 31 determines (or judges) the predetermined pulse width and the predetermined level. With such a scheme, a malfunction caused by a noise or the like can be reduced. In this manner, the DC blocking and clipping circuit 31 may have a function to determine a CLK 73 for LUT as a readout signal.

Further, transmission signals are sent out via the transmission and reception signal line 11A to the plurality of C-MUTs 8a to 8d. Therefore, the transmission signals are applied onto the plurality of C-MUTs 8a to 8d through the opened gate circuit.

Again, after the transmission time period Tb in FIG. 11(B), a CLK 73 for LUT is sent out at the start of the reception time period Tc, and thereby the LUT 63 selects a C-MUT as an ultrasound transducer for reception.

Examples of set patterns of C-MUTs stored in the LUT 63 of FIG. 10 and selectively used for transmission and reception are shown in tables of FIGS. 12(A) and 12(B).

CLK Nos. in the tables of FIGS. 12(A) and 12(B) indicate the CLKs 73 for LUT shown in FIG. 11(B) and inputted into the LUT 63 of FIG. 10. The set pattern A in FIG. 12(A) shows the case in which each ultrasound transducer is selected and used for transmission or reception. Also in a scheme that uses the LUT 63, such setting of the set pattern A allows ultrasound transducers to be changed over one by one.

Further, the set pattern B in FIG. 12(B) shows the case in which a plurality of ultrasound transducers are used for transmission. The plurality of C-MUTs to be selected and used are registered for a same (one) CLK No., and thereby ultrasound can be transmitted by the plurality of ultrasound transducers. Further, FIG. 12(B) shows an example in which the ultrasound transducers are changed over one after another at the time of reception.

In this manner of the present embodiment, before ultrasound is actually transmitted and received, if an ultrasound transducer to be driven which is used to transmit and receive ultrasound is linked with a clock number and registered on (stored in) the LUT 63, ultrasound can be transmitted and received by one or more ultrasound transducers.

That is, in the present embodiment, as selection signals, a selection signal for transmission and a selection signal for reception that allow separately setting an ultrasound transducer selected for transmission and an ultrasound transducer selected for reception are stored in the LUT 63, so as to enable an ultrasound transducer used for transmission and an ultrasound transducer used for reception to be changed.

In addition, as shown in FIG. 12(B), a plurality of ultrasound transducers may be selected at a time to transmit ultrasound. In this manner, a plurality of ultrasound transducers are selected at a time to transmit ultrasound, and thereby ultrasound with large signal strength can be transmitted. In this case, a reception signal with a high S/N can be obtained. Therefore, an ultrasound tomographic image with a high image quality can be displayed.

In the configuration illustrated in FIG. 10, a counter (e.g., as the OSC portion 64) that counts the number of the inputted CLKs 73 for LUT is installed in the selection circuit 62, and the number of the CLKs 73 for LUT counted by the counter may be used to identify a CLK No. shown in FIG. 12.

Then, a count value corresponding to a CLK No. from the counter may be applied to the LUT 63 as an address signal and data of a selection signal linked with the count value and stored in the LUT 63 may be read out from the LUT 63. That is, the counter may be used as a signal generating portion.

It should be noted that a method for storing a selection signal in the LUT 63 is not limited to the method shown in FIG. 11(A); data of a selection signal may also be stored in the LUT 63 by other means. For example, a data writing device such as a ROM writer may be used to write in advance a transducer selection code 71 into a ROM used as the LUT 63, and the ROM in which the transducer selection code 71 is written may be used as the LUT 63.

In addition, the foregoing example has described the case in which the two-electrode-type C-MUT 8$i$ shown in FIG. 1 is used, but the foregoing example may be applied to the case of the three-electrode-type C-MUTs described in the second embodiment.

Figure 13:
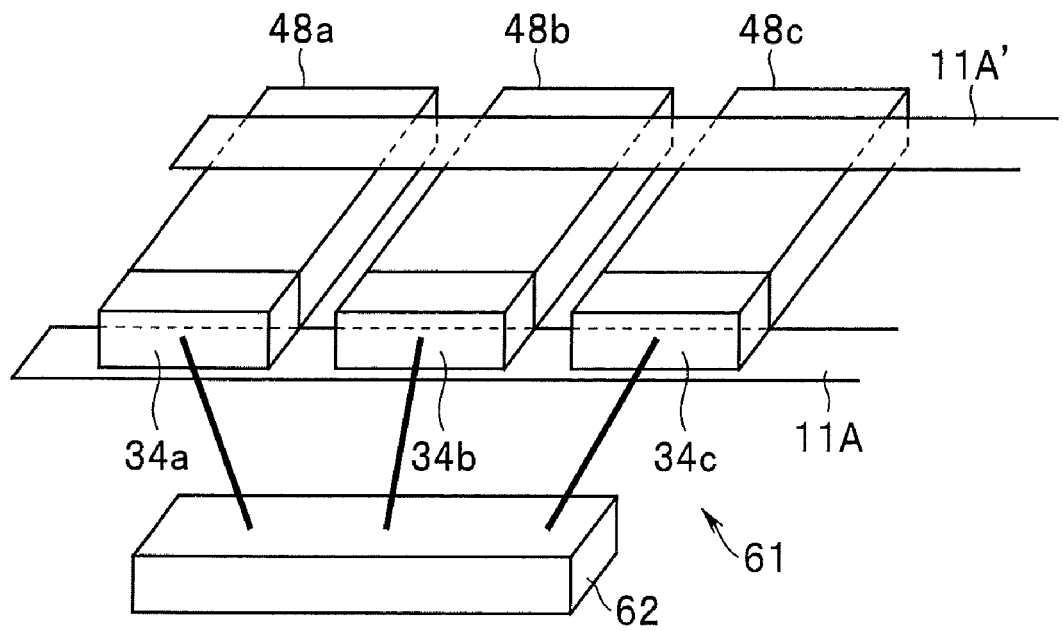
FIG. 13 is a diagram illustrating a configuration around the signal determining portion in which the third embodiment is applied to three-electrode-type capacitive ultrasound transducers (C-MUTs).

FIG. 13 illustrates a configuration around the signal determining portion 61 in which the third embodiment is applied to the three-electrode-type C-MUTs 48$a$ to 48$c$.

The gate circuits 34$a$ to 34$c$ contiguous to the C-MUTs 48$a$ to 48$c$ are on the transmission and reception signal line 11A, and the selection circuit 62 is also connected with the gate circuits 34$a$ to 34$c$.

As described above, a plurality of ultrasound transducers are selected to transmit ultrasound, and thereby comparatively large ultrasound can be emitted to an object to be examined, so that the sensitivity to receive ultrasound can be increased.

Furthermore, if a ultrasound transducer to be selected is stored in the LUT 63 as data in advance, it is not necessary to insert a long code between transmission and reception; for example, the insertion of one pulse will suffice. Thus, a time period having CLKs 73 for LUT to select a transducer can be shortened, and as a result, a frame rate in an ultrasound tomographic image for one screen (one frame) can be increased.

Additionally, as in the first embodiment, since the transmission and reception signal line 11A also functions as a selection signal line, the number of signal lines needed to be inserted into the ultrasound probe 2 can be reduced. Therefore, for example, an outer diameter of the insertion portion can be reduced, so that advantageously, the present embodiment can be applied to wider use.

Fourth Embodiment

In the foregoing embodiments, the case in which C-MUTs are used as ultrasound transducers has been described. The present invention is not limited to the case in which the ultrasound transducers are C-MUTs. The present invention may also be applied to ultrasound transducers formed by using piezoelectric elements (hereinafter, referred to as the piezoelectric transducers).

Figure 14:
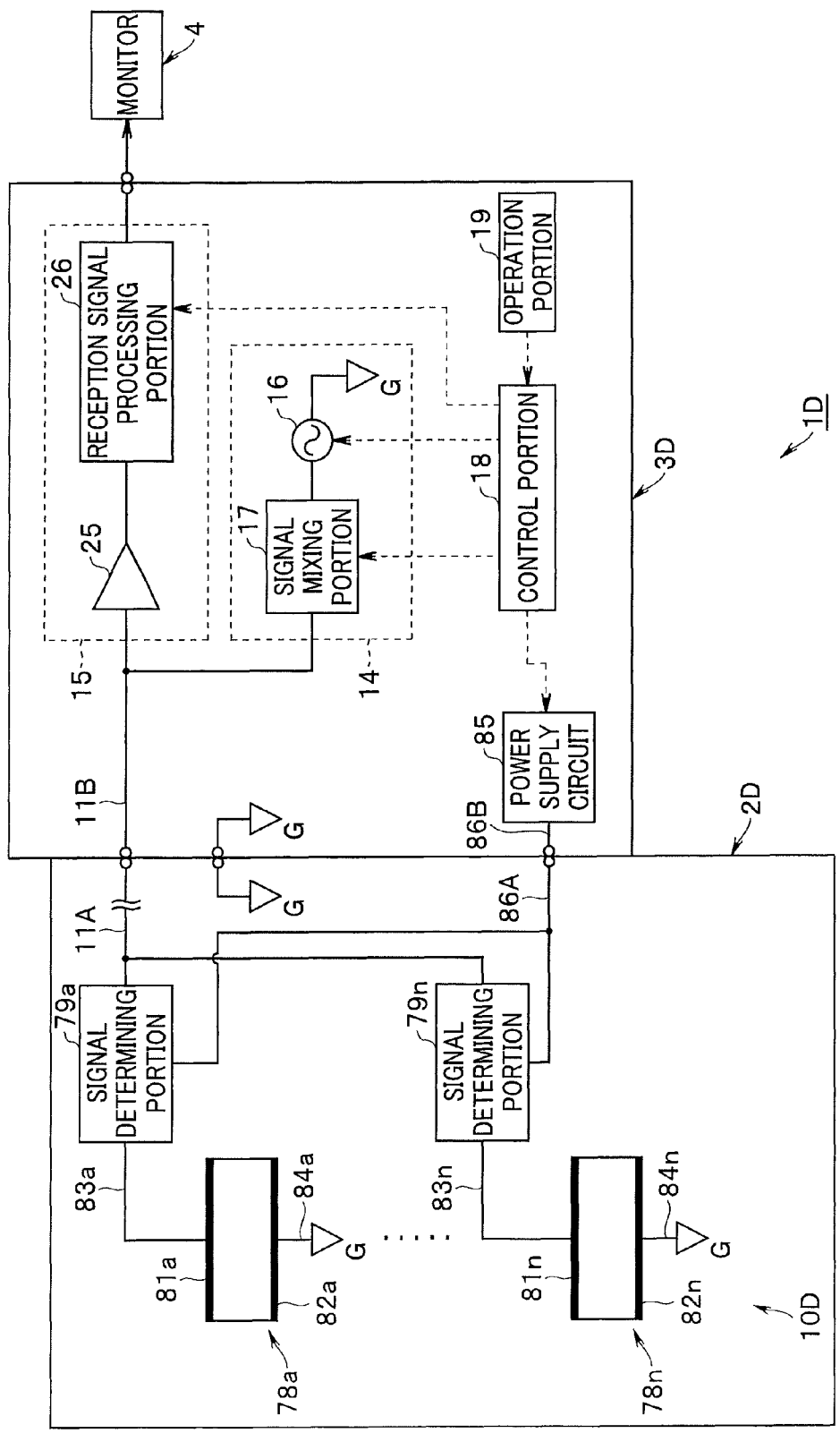
FIG. 14 is a block diagram illustrating a configuration of an ultrasound diagnostic apparatus of a fourth embodiment of the present invention.

An ultrasound diagnostic apparatus 1D of a fourth embodiment shown in FIG. 14 uses, for example, PZT as piezoelectric transducers.

The ultrasound diagnostic apparatus 1D illustrated in FIG. 14 includes an ultrasound probe 2D, an observing apparatus 3D, and a monitor 4. It should be noted that the ultrasound probe 2D and the observing apparatus 3D in the present embodiment have the same configurations as those in FIG. 1. Therefore, also in the present embodiment, a transmission and reception signal line 11A and a ground line connected with ground terminal are inserted into an insertion portion 5 of the ultrasound probe 2D. In the present embodiment, a power supply line 86A is inserted into the insertion portion 5 as described later.

In the ultrasound probe 2D, lead zirconate titanate (abbreviated as PZT) 78$i$ is used as piezoelectric elements instead of the C-MUT 48$i$ in the ultrasound probe 2B shown in FIG. 7.

One electrode 81$i$ of each PZT 78$i$ constituting the ultrasound transducer array 10D is connected with one end of a signal determining portion 79$i$ via a signal line 83$i$, and the other end of the signal determining portion 79$i$ is connected with the common transmission and reception signal line 11A.

The other electrode 82$i$ of the PZT 81$i$ is connected with the ground via a signal line 84$i$.

Further, because the observing apparatus 3D does not need a DC bias in the observing apparatus 3B shown in FIG. 7, the DC bias outputting portion 12 is removed and a power supply circuit 85 is included.

That is, the observing apparatus 3D includes a transmitting portion 14 and a receiving portion 15 connected with one end of the transmission and reception signal line 11B, the other end of which is connected with a transmission and reception signal line 11A, a control portion 18 that controls the transmitting portion 14 and the receiving portion 15, and an operation portion 19.

Further, a power supply line 86B in the observing apparatus 3D is connected with one end of the power supply line 86A in the ultrasound probe 2D and the power supply circuit 85 supplies power supply (power) for operation to the signal determining portion 79$i$, with which the other end of the power supply line 86A is connected. The configuration of the signal determining portion 79$i$ is similar to that in FIG. 9. However, the signal determining portion 79$i$ is supplied with the power supply for operation via the power supply line 86A.

The others are similar to those shown in FIG. 7. An operation of the present embodiment is as follows.

The transmission signal outputting portion 16 outputs a transmission signal, and the signal mixing portion (signal superimposing portion) 17 mixes the transmission signal with a selection signal and transmits the signal to the signal determining portion 79$i$ via the transmission and reception signal line 11A.

Each signal determining portion 79$i$ determines by the selection signal whether or not the transmission signal is for a PZT 78$i$ selected by the selection signal, and if it is determined that the transmission signal is for the selected PZT 78$i$, the transmission signal is applied onto the PZT 78$i$.

Then, the PZT 78$i$ transmits ultrasound. The transmitted ultrasound is reflected from a part in which acoustic impedance is changed, received by the PZT 78$i$ used for the transmission, and converted into an ultrasound signal.

The ultrasound signal passes through the signal determining portion 79*i* and the transmission and reception signal lines 11A and 11B, and is amplified by the amplifier portion 25. Then, the amplified signal is imaged at the reception signal processing portion 26 and displayed on the monitor 4.

The power for the signal determining portion 79*i* is supplied from the power supply circuit 85 via the power supply lines 86B and 86A.

Figure 15:
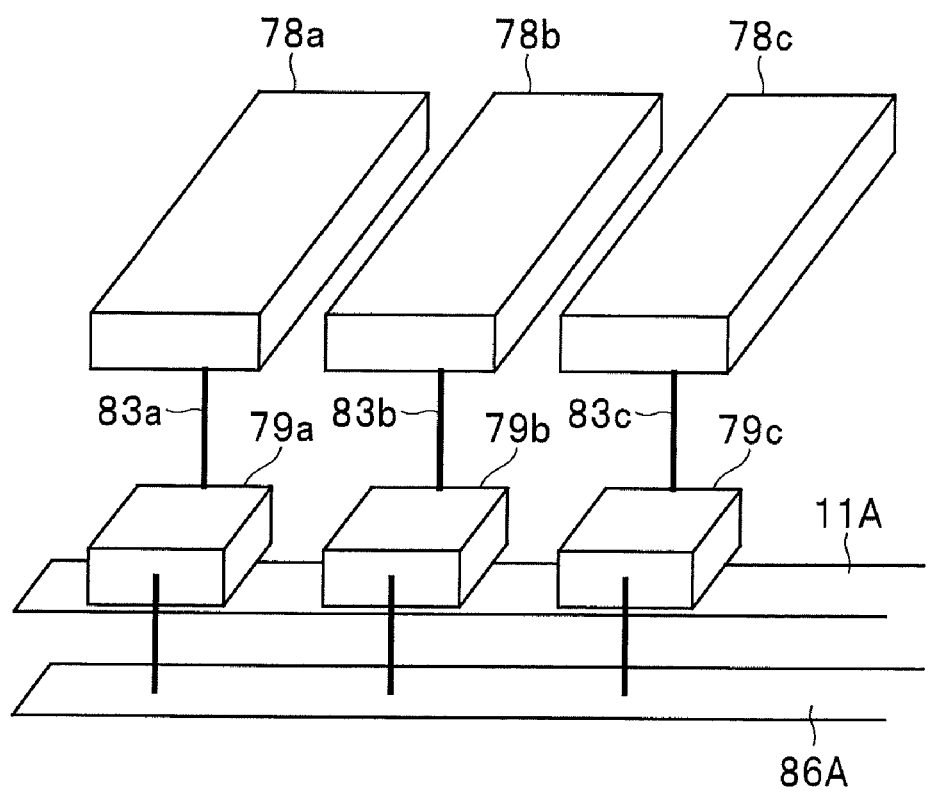
FIG. 15 is a diagram illustrating an example of a configuration around a signal determining portion in the fourth embodiment.

FIG. 15 illustrates an example of a configuration of, for example, three PZTs 78*a* to 78*c* and signal determining portions 79*a* to 79*c*. The signal determining portions 79*a* to 79*c* are connected with the PZTs 78*a* to 78*c*, respectively, and the signal determining portions 79*a* to 79*c* are connected with the common transmission and reception signal line 11A.

Besides the transmission and reception signal line 11A, the power supply line 86A is provided to operate the signal determining portions 79*a* to 79*c*. A configuration of the signal determining portion 79*i* is identical to the three-electrode-type configuration shown in FIG. 9, and because the present embodiment does not need the supply of a DC bias, a selection signal is taken out of a transmission signal by a clipping circuit (51*i*, if denoted by the same reference numeral in FIG. 9).

As in the first embodiment, also in the present embodiment, a transducer can be selected by the signal determining portion 79*i* with the transmission and reception signal line 11A also functioning as a selection signal line. Therefore, the number of signal lines needed to be inserted into the ultrasound probe 2D can be reduced. In addition, for example, an outer diameter of the insertion portion can be reduced, so that advantageously, the present embodiment can be applied to wider use.

Figure 11:
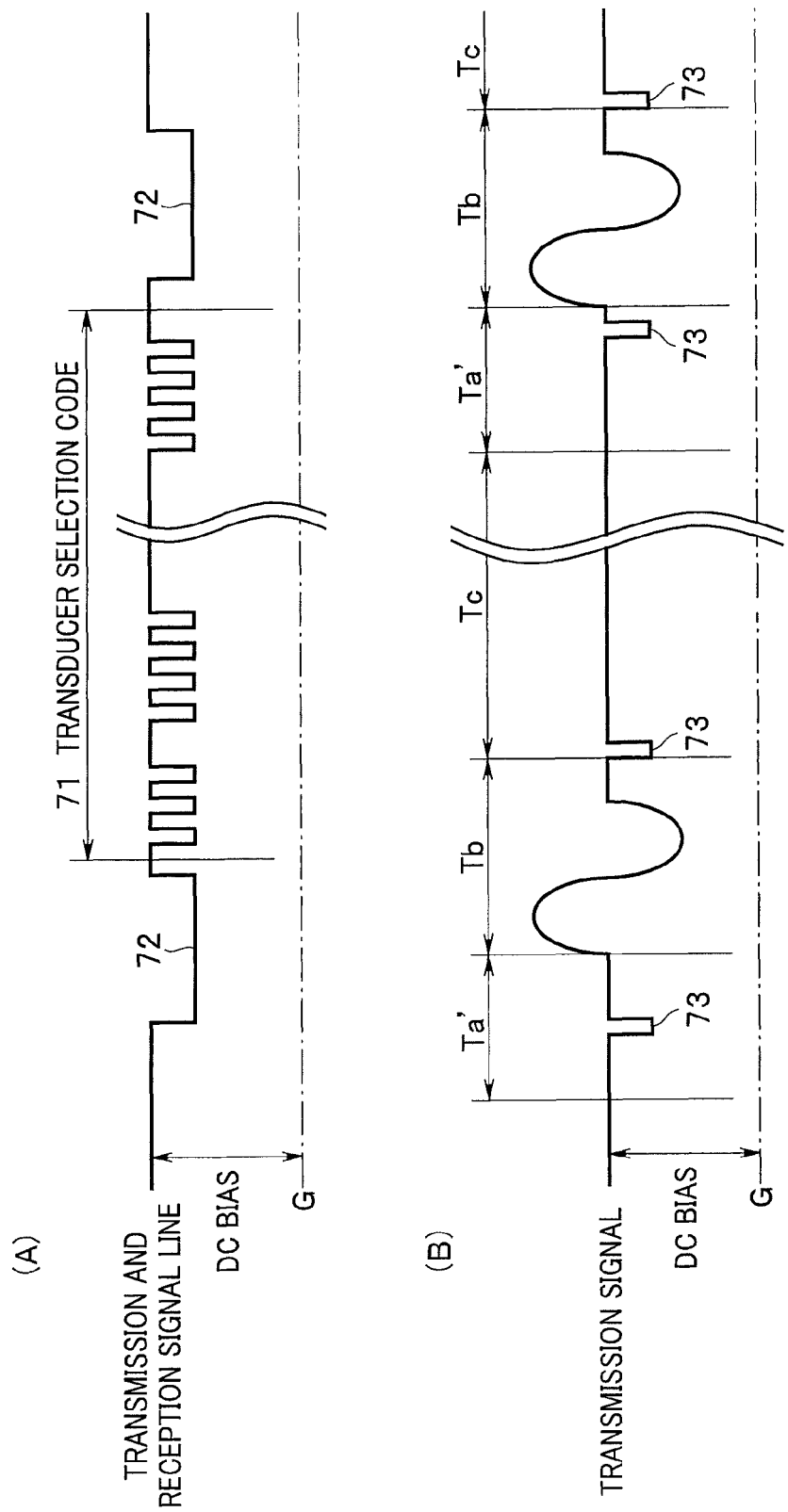
FIG. 11 is an explanation diagram of an operation of storing a selection signal into a look-up table (LUT) via a transmission and reception signal line in the third embodiment and an operation of mixing a clock for LUT with a transmission signal to select an ultrasound transducer.

Further, the transducer selection circuit scheme using the LUT 63 and being shown in FIG. 10 and FIG. 11 can be applied as selecting means in which piezoelectric transducers are used.

In all the above-described embodiments, as means for selecting a transducer, pulse counting has been used, but as other means, a cycle and the number of a sinusoidal signal may be changed and judged. Also, in place of the gate circuit, for example, a semiconductor switch or other switches that can be switched on/off by a control signal may also be used.

It should be noted that an embodiment formed by partly adopting some of the above-described embodiments belongs to the present invention.

What is claimed is:

1. An ultrasound diagnostic apparatus comprising:
a plurality of ultrasound transducers;
transmission and reception signal lines configured to send transmission and reception signals for transmitting and receiving ultrasound to the plurality of ultrasound transducers;
signal determining portions that are provided adjacent to the plurality of ultrasound transducers and are configured to determine a selection signal for selecting an ultrasound transducer to be driven or a readout signal for reading out the selection signal, the selection signal being sent out in synchronization with a transmission signal for forming the transmission and reception signal, and electrically couple the ultrasound transducer to be driven with the transmission and reception signal line in accordance with a result of the determination; and
direct current blocking/clipping circuits that are provided in the signal determining portions, configured to block a direct current bias component superimposed on the transmission and reception signal and sent via the transmission and reception signal line, and clip a waveform,
wherein the transmission and reception signal line is configured to send the transmission and reception signal with the selection signal or the readout signal, and
wherein the direct current blocking/clipping circuit is configured to separate and extract the selection signal or the readout signal superimposed at a position before a signal waveform of the transmission signal which is transmitted through the transmission and reception signal line.

2. The ultrasound diagnostic apparatus according to claim 1, wherein
the transmission and reception signal line superimposes the transmission signal on the selection signal or the readout signal placed before the signal waveform of the transmission signal and sends a resultant signal.

3. The ultrasound diagnostic apparatus according to claim 1, wherein
the signal determining portion further includes a pulse counter that counts a number of pulses forming the selection signal for selecting the ultrasound transducer to be driven, and
the signal determining portion determines the ultrasound transducer to be driven in accordance with the number of the pulses counted by the pulse counter.

4. The ultrasound diagnostic apparatus according to claim 1, wherein
the signal determining portion further includes:
a pulse counter that counts a number of pulses forming the selection signal for selecting the ultrasound transducer to be driven;
a judging portion that judges the ultrasound transducer to be driven according to the number of the pulses counted by the pulse counter; and
a gate circuit that opens and closes to apply the transmission signal onto the ultrasound transducer to be driven.

5. The ultrasound diagnostic apparatus according to claim 4, wherein
the gate circuit switches from closed to open so as to apply the transmission signal to the ultrasound transducer to be driven in response to a control signal from the judgement of the judging portion.

6. The ultrasound diagnostic apparatus according to claim 1, wherein
the signal determining portion comprises:
the direct current blocking/clipping circuit;
a selection look-up table portion in which the selection signal for selecting an ultrasound transducer that performs transmission and reception is stored in advance; and
a signal generating portion that generates a signal for reading out data of the selection signal from the selection look-up table portion.

7. The ultrasound diagnostic apparatus according to claim 6, wherein
the selection look-up table portion stores, as the selection signals, a selection signal for transmission and a selection signal for reception that allow separately setting an ultrasound transducer selected for transmission and an ultrasound transducer selected for reception to enable an ultrasound transducer used for transmission and an ultrasound transducer used for reception to be changed.

8. The ultrasound diagnostic apparatus according to claim 1, wherein
the plurality of ultrasound transducers are formed with capacitive ultrasound transducers.

9. The ultrasound diagnostic apparatus according to claim 1, wherein
the signal determining portion includes a data storage portion storing selection signal data for, by using the readout signal superimposed before the signal waveform of the transmission signal and sent via the transmission and reception signal line, selecting an ultrasound transducer to be driven corresponding to the readout signal.

10. The ultrasound diagnostic apparatus according to claim 1, wherein
the plurality of ultrasound transducers and the signal determining portions are provided at a distal end portion of an elongate insertion portion, and the transmission and reception signal line inserted into the insertion portion is, via a connector, detachably connected with an observing apparatus including a transmitting portion that generates the transmission signal and a receiving portion that performs signal processing on a reception signal received by the plurality of ultrasound transducers.

11. The ultrasound diagnostic apparatus according to claim 10, wherein
the observing apparatus includes a signal superimposing portion that superimposes the selection signal or the readout signal on the transmission signal and before the signal waveform of the transmission signal.

12. The ultrasound diagnostic apparatus according to claim 9, wherein
the data storage portion stores the selection signal data that allows selecting one or more ultrasound transducers as an ultrasound transducer to be driven corresponding to a single pulse for forming the readout signal.

13. The ultrasound diagnostic apparatus according to claim 1, wherein
the signal determining portion includes a voltage converting circuit that converts a direct current bias component superimposed on the transmission signal and sent, into a predetermined power supply voltage for operating the signal determining portion.

14. An ultrasound diagnostic apparatus comprising:
a plurality of ultrasound transducers;
transmission and reception signal lines configured to send transmission and reception signals for transmitting and receiving ultrasound to the plurality of ultrasound transducers; and
signal determining portions that are provided adjacent to the plurality of ultrasound transducers and are configured to determine a selection signal for selecting an ultrasound transducer to be driven, the selection signal being sent out in synchronization with a transmission signal for forming the transmission and reception signal, and electrically couple the ultrasound transducer to be driven with the transmission and reception signal line in accordance with a result of the determination,
wherein the signal determining portion includes: a clipping circuit configured to clip a signal waveform of the transmission signal; a pulse counter configured to count a number of pulses for forming the selection signal for selecting the ultrasound transducer to be driven; a judging portion configured to judge the ultrasound transducer to be driven using the number of the pulses counted by the pulse counter; and a gate circuit configured to open and close by a control signal of the judgement from the judging portion to apply the transmission signal to the ultrasound transducer to be driven, and
wherein the transmission and reception signal line sends the transmission and reception signal with the selection signal.

15. The ultrasound diagnostic apparatus according to claim 14, wherein
the plurality of ultrasound transducers are formed with ultrasound transducers in which piezoelectric elements are used.

16. The ultrasound diagnostic apparatus according to claim 14, wherein
the plurality of ultrasound transducers are formed with capacitive ultrasound transducers using two electrodes, between which a cavity is made, and a third electrode facing the two electrodes and connected with a ground line in the transmission and reception signal lines, and the two transmission and reception signal lines except for the ground line send the separated transmission and reception signal to one of the two electrodes and a DC bias voltage to the other electrode.

* * * * *